United States Patent
Jablonski et al.

(10) Patent No.: US 9,766,237 B2
(45) Date of Patent: Sep. 19, 2017

(54) METHOD OF CAPTURING BACTERIA ON POLYLYSINE-COATED MICROSPHERES

(71) Applicant: Iris International, Inc., Chatsworth, CA (US)

(72) Inventors: Edward Jablonski, Escondido, CA (US); Carl Hulle, Encinitas, CA (US)

(73) Assignee: Iris International, Inc., Chatsworth, CA (US)

( * ) Notice: Subject to any disclaimer, the term of this patent is extended or adjusted under 35 U.S.C. 154(b) by 0 days.

(21) Appl. No.: 14/776,637

(22) PCT Filed: Mar. 13, 2014

(86) PCT No.: PCT/US2014/026608
§ 371 (c)(1),
(2) Date: Sep. 14, 2015

(87) PCT Pub. No.: WO2014/151879
PCT Pub. Date: Sep. 25, 2014

(65) Prior Publication Data
US 2016/0033503 A1     Feb. 4, 2016

Related U.S. Application Data

(60) Provisional application No. 61/801,508, filed on Mar. 15, 2013.

(51) Int. Cl.
*G01N 33/569*     (2006.01)
*G01N 33/543*     (2006.01)
*C08G 69/10*     (2006.01)
*C08L 77/04*     (2006.01)
*G01N 33/544*     (2006.01)

(52) U.S. Cl.
CPC ....... *G01N 33/56911* (2013.01); *C08G 69/10* (2013.01); *C08L 77/04* (2013.01); *G01N 33/544* (2013.01); *G01N 33/54313* (2013.01); *G01N 33/54393* (2013.01); *G01N 33/56938* (2013.01); *G01N 2469/10* (2013.01)

(58) Field of Classification Search
CPC .............................................. G01N 33/54313
See application file for complete search history.

(56) References Cited

U.S. PATENT DOCUMENTS

2009/0325258 A1    12/2009   Matsunaga et al.

FOREIGN PATENT DOCUMENTS

EP    1 108 743 A2    6/2001
EP    1 108 743 A3    6/2001

OTHER PUBLICATIONS

Ward, et al. Blood, 2001, 97:2221-2229.*
Anonymous "Sulfo-SMCC 22322 22360—Pierce Instructions," Piercenet.com, located at http:jjwww.piercenet.comjfilesj0581as4.pdf, Nov. 2003, 4 pages.
Anonymous "SATA and SATP 26102 26100—Thermo Scientific Instructions," Piercenet.com, located at http://www.piercenet.comjinstructions/2160126.pdf, Jun. 28, 2011, 5 pages.
Binnerts et al. "Visualization of the nucleoid in living bacteria on poly-lysine coated surfaces by the immersion technique," Journal of Microscopy, Mar. 1982, vol. 125, Pt. 3, pp. 359-363.
Sieving et al. "Preparation and Characterization of Paramagnetic Polychelates and Their Protein Conjugates," Bioconjugate Research, 1990, vol. 1., No. 1, pp. 65-71.
Singh et al."Poly L-lysine-coated albumin nanoparticles: Stability, mechanism for increasing in vitro enzumatic resilience, and siRNA release characteristics," Acta Biomaterialia, 2010, No. 6, pp. 4277-4284.
Trubetskoy et al. "Chemically Optimized ANtimyosin Fab Conjugates with Chelating Polymers: Importance of the Nature of the Protein-Polymer Single Site Covalent Bond for Biodistribution and Infraction Localization," Jul./Aug. 1993, vol. 4, No. 4, pp. 251-255.
Invitation to Pay Additional Fees dated Jul. 14, 2014 for PCT Patent Application No. PCT/US2014/026608, 6 pages.
International Search Report and Written Opinion dated Sep. 16, 2014 for PCT Patent Application No. PCT/US2014/026608, 18 pages.

* cited by examiner

*Primary Examiner* — Bin Shen
(74) *Attorney, Agent, or Firm* — Kilpatrick Townsend & Stockton LLP

(57) ABSTRACT

The present disclosure relates to compositions, methods, and kits for the detection, separation and/or isolation of microorganisms. Specifically, the disclosure relates to compositions, methods, and kits for using polylysine-coated particles to capture microorganisms such as bacteria.

20 Claims, No Drawings

METHOD OF CAPTURING BACTERIA ON POLYLYSINE-COATED MICROSPHERES

CROSS-REFERENCES TO RELATED APPLICATIONS

This application is a national stage entry of PCT/US2014/026608, filed Mar. 14, 2014, which claims priority to U.S. Provisional Patent Application No. 61/801,508, filed Mar. 15, 2013 and entitled "Method of Capturing Bacteria on Polylysine-Coated Microspheres," both applications are herein incorporated by reference in their entirety for all purposes.

FIELD OF THE INVENTION

The present disclosure relates to compositions, methods, and kits for the detection, separation and/or isolation of microorganisms. Specifically, the disclosure relates to compositions, methods, and kits for using polylysine-coated microspheres to capture microorganisms such as bacteria.

BACKGROUND

Microorganisms such as bacteria and viruses in biological samples are hard to detect at low concentrations and usually require long induction or incubation times before further analysis can be performed. Currently, the identification of microorganisms in biological samples is a time-consuming process. For bacterial detection, body fluid samples must be incubated for long periods of time before any bacterial cultures can be positively identified. Methods that can detect bacteria at ultralow concentrations without time-consuming incubation or amplification processes thus have certain advantages in clinical diagnosis, food safety, biodefense, and/or environmental monitoring applications.

Currently, the identification of bacteria in urine is a time-consuming process. Urine samples must be incubated for days before positive identification of any bacterial cultures can be identified.

SUMMARY OF THE INVENTION

The instant disclosure is directed to a novel approach which uses polylysine-coated microspheres to capture and detect microorganisms and/or pathogens at very low concentrations. Accordingly, the present disclosure provides methods and compositions useful in minimizing the time needed to positively identify the presence of microorganisms such as bacteria in biological samples to a near "real-time" event. The disclosure provides compounds, compositions and methods of making and using the compounds and to attract and immobilize bacteria on a solid support matrix. This solid support matrix, in turn, can be concentrated (thus concentrating the microbes such as bacteria) leading to positive and rapid identification of bacteria within a short time after obtaining the sample. This disclosure provides provide specific and efficient methods for microbial separation and/or detection.

In one aspect, the present disclosure relates to compositions comprising poly-L-lysine coated microspheres, as well as kits comprising the microspheres, and methods of their use for the detection, affinity separation, enrichment, and/or reducing the concentration of microorganisms, for example, pathogens, in a sample. The microspheres may include functionalized protein microspheres, or functionalized magnetic particles, where the functional groups are capable of binding to said microorganisms via ligand-receptor, antibody-antigen, ionic, or metal-ligand interaction.

The present disclosure also provides for a kit for detecting or reducing pathogens in a sample, comprising a receptacle or compartment containing an appropriate amount of functionalized solid supports coated with poly-L-lysine, which are capable of binding to said microbes and/or pathogens. In some aspects, the solid supports are beads or particles, which can include, for example, microspheres or nanoparticles. In some aspects, the beads and particles such as microspheres or nanoparticles may be magnetic.

In one aspect, the present disclosure provides a synthetic polymer of the general formula (I):

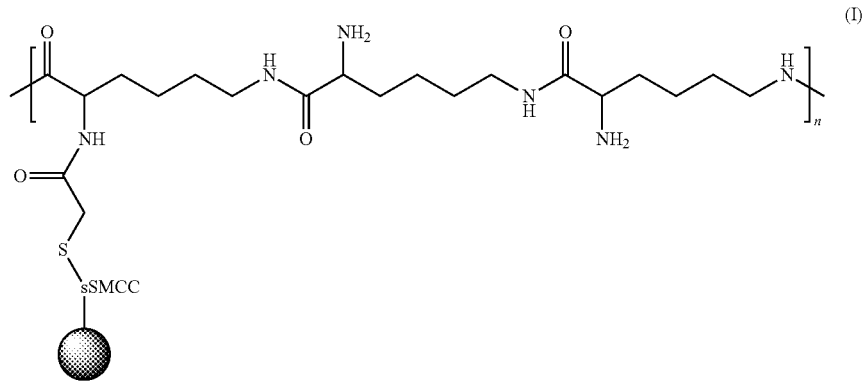

wherein n is 10 to 100, where the synthetic polymer of formula (I) comprises repeating monomer units of polylysine wherein the polymer can form a complex with a solid support and said polymer-solid support complex is effective in binding microorganism. In one embodiment, the linker is Succinimidyl-4-(N-maleimidomethyl)cyclohexane-1-carboxylate (sSMCC). In one embodiment, the solid support comprises microspheres, which may be protein microspheres.

In one aspect, the disclosure provides a method for capturing microorganisms in a test sample comprising:
a) adding a synthetic polymer comprising repeating monomer units of polylysine to a solution comprising the microorganisms and a fluorescent stain;
b) agitating the mixture from step a) followed by incubation;
c) washing the mixture from step b) by centrifugation;
d) removing the microspheres from step c); and e) visually inspecting the microspheres from step d) for the presence of any colony forming units.

In one embodiment, the microorganisms are gram positive bacteria. In one embodiment, the microorganisms are gram negative bacteria. In one embodiment, the microorganisms are selected from *Staphylococcus epidermidis*, *Streptococcus gallolyticus*, *Escherica coli*, and *Proteus mirabilis*. In one embodiment, the linker is succinimidyl-4-(N-maleimidomethyl)cyclohexane-1-carboxylate (sSMCC). In one embodiment, the fluorescent stain is a green fluorescent nucleic acid stain. In one embodiment, the solid support comprises microspheres. In one embodiment, the microspheres comprise a coating of human serum albumin.

In one aspect, the present disclosure provides a process for preparing a synthetic polymer of general formula (I) comprising the steps:

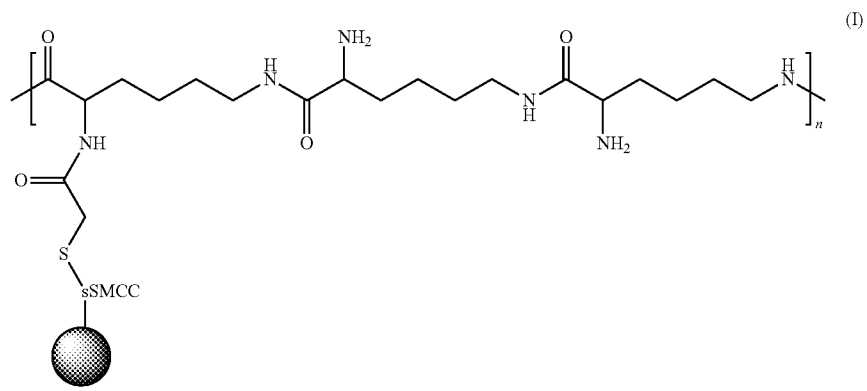

(I)

wherein n is 10 to 100, a) reacting polylysine with (N-succinimidyl S-acetylthioacetate) (II) to give the compound of formula (III):

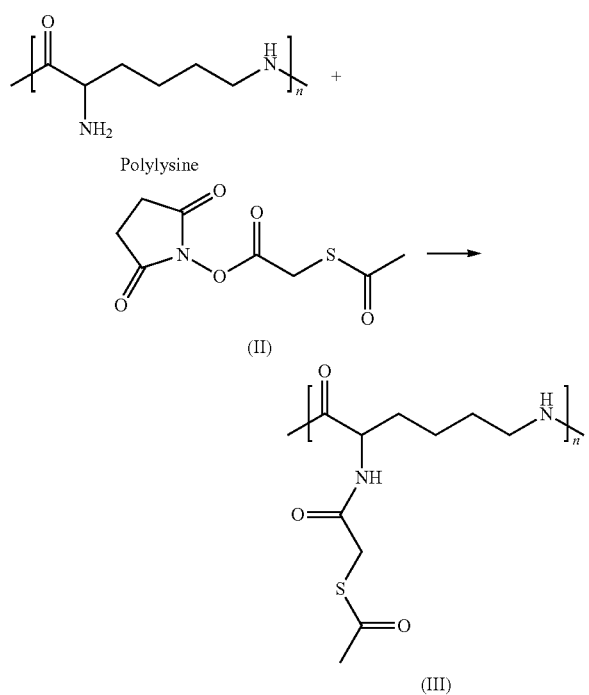

b) reacting the compound of formula (III) from step a) with a deprotecting agent to give the compound of formula (IV):

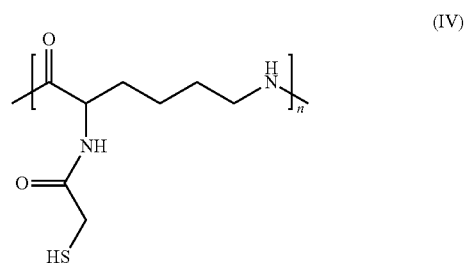

(IV)

c) reacting succinimidyl-4-(N-maleimidomethyl)cyclohexane-1-carboxylate (sSMCC) with human serum albumin coated microspheres to produce the compound of formula (V):

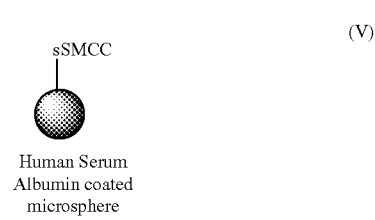

(V)

Human Serum Albumin coated microsphere d) reacting the compound of formula (IV) from step b) with the compound of formula (V) from step c) to produce synthetic polymer (I).

In one embodiment, the deprotecting agent is hydroxylamine hydrochloride.

In one aspect, the present disclosure provides a method of detecting a species in a sample, comprising the steps of:

(a) providing, in a solution, functionalized microspheres comprising Poly-L-Lysine;

(b) contacting, in the sample, the functionalized microspheres with the species, thereby generating microsphere/species complexes;

(c) separating the functionalized microsphere-species complexes in said sample; and (d) detecting the presence of the complexes between said species and said functionalized microsphere wherein presence of said complexes indicate the presence of said species in the sample.

In one aspect, the present disclosure provides a method of concentrating or depleting a species in a sample, comprising the steps of:
(a) providing, in a solution, functionalized microspheres comprising Poly-L-lysine;
(b) contacting, in the sample, the functionalized microspheres with the species, thereby generating microspheres/species complex;
(c) separating the functionalized microsphere-species complexes in said sample; and
(d) detecting the presence of the complexes between said species and said functionalized microsphere wherein presence of said complexes indicate the presence of said species in the sample.

In certain embodiments, the microspheres are magnetic microspheres and the separating is achieved by aggregation of the microsphere-species complex under a magnetic field. In certain embodiments, the PLL is attached to the microsphere via an avidin or streptavidin linkage. In certain embodiments, the sample is a liquid selected from any of the following: body fluids; urine, blood, serum, plasma, spinal fluid, synovial fluid, saliva, urine, semen, cell and/or tissue homogenates. In certain embodiments, the sample contains a species of a bacterium. In certain embodiments, the species is a gram-positive bacterium. In certain embodiments, the species is a gram-negative bacterium. In certain embodiments, the bacterium is *Staphylococcus* or *Enterococcus*.

In one aspect, the present disclosure provides a composition for detecting a species in a sample, comprising:
a microsphere comprising Poly-L-Lysine;
wherein upon contacting, in the sample, the functionalized microsphere forms a microsphere-species complex.

In one aspect, the present disclosure provides a composition for concentrating or depleting a species in a sample, comprising:
a microsphere comprising Poly-L-Lysine;
wherein upon contacting, in the sample, the functionalized microsphere forms a microsphere-species complex.

In certain embodiments, the microspheres are magnetic microspheres and the separating is achieved by aggregation of the microsphere-species complex under a magnetic field.

In certain embodiments, the PLL is attached to the microsphere via an avidin or streptavidin linkage. In certain embodiments, the sample is a liquid from a body fluid selected from the group consisting of blood, serum, plasma, spinal fluid, synovial fluid, saliva, urine, semen, cell and/or tissue homogenates. In certain embodiments, the molecular weight of the poly-L-lysine is from about 4200 to about 130,000 kd. In certain embodiments, the molecular weight of the poly L-lysine is about 68000 kd.

In one aspect, the present disclosure provides a kit comprising the polymer of claim 1 and instructions for use.

Additionally, this disclosure provides a device which is configured to perform the method for detecting or reducing microorganisms, comprising any of the above methods.

DETAILED DESCRIPTION OF THE INVENTION

In general, there are two strategies to fabricate magnetic or non-magnetic microparticle-based multifunctional structures. The first strategy is molecular functionalization. Functional molecules (e.g., antibodies, ligands, or receptors) can be used to coat the magnetic or non-magnetic microparticles and make them interact with a biological entity with high affinity, thus providing a controllable means of "tagging". After molecular functionalization, the functional magnetic or non-magnetic microparticles such as exemplary microspheres can confer high selectivity and sensitivity for many biological applications. The second general strategy for fabrication is to combine magnetic or non-magnetic nano- or micromaterials and other functional structures by sequential coating, which produces a single entity conferring multiple functions in nano- or micro-scale. Exemplary preparations of particles have been reported previously, including for example, U.S. Pat. No. 7,754,444.

The present disclosure provides novel compound, compositions, and methods of use comprising various molecules of poly-L-lysine which can be attached to a solid surface via streptavidin/biotin linkages, said compound, composition, and methods are useful for separation, detection, concentration depletion and/or purification of microorganisms. The disclosure is generally based at least in part on the surprising and unexpected discovery that compound and composition comprising poly-L-lysine moieties or poly-L-lysine like moieties can be modified to attach to a small solid surface which form a complex and be subject to manipulation in situ. The manipulation of the solid surface allows for the detection, capture, concentration, depletion, separation and identification of the exemplary microorganisms in a sample (e.g. bacteria).

The exemplary compound and compositions described herein can comprise various components listed below in accordance with the exemplary embodiments of the present disclosure. These include:

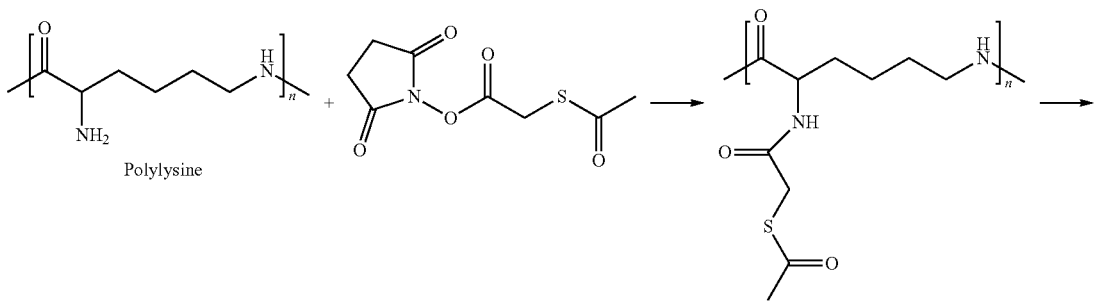

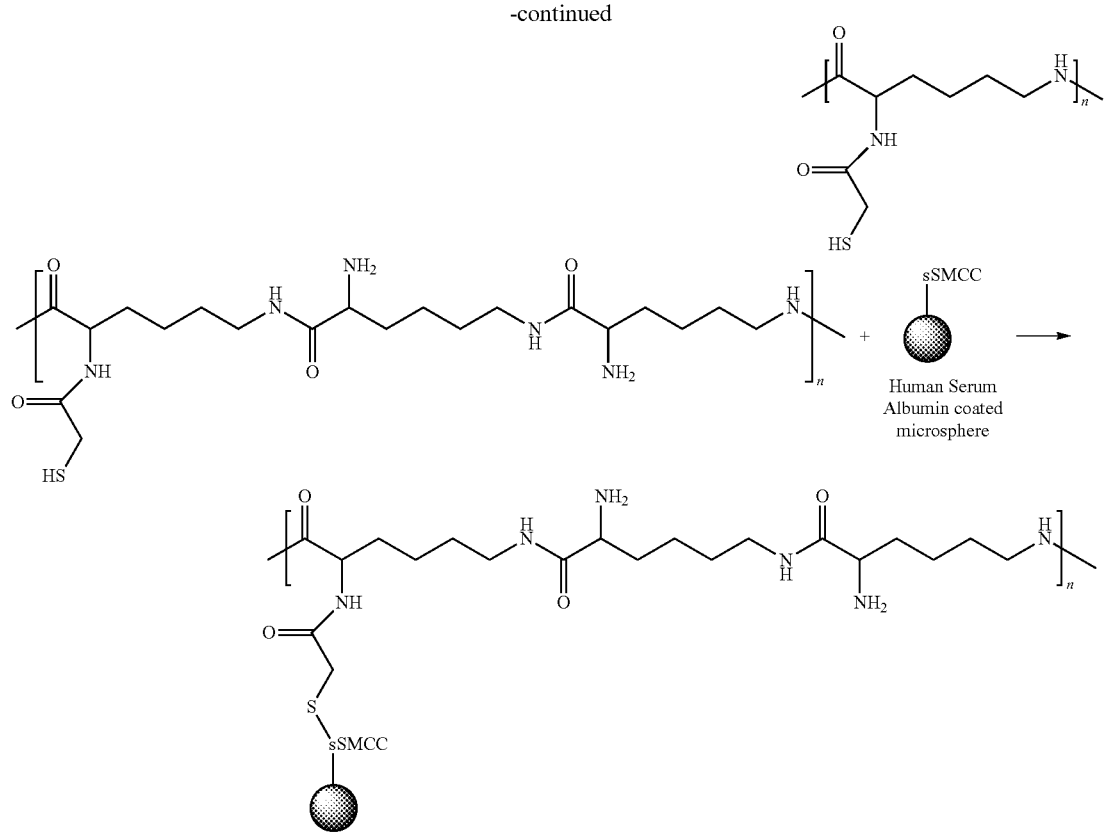

1) Exemplary suitable Poly-L-lysine. As an example, polylysine can be used to attach to an exemplary solid support (e.g. microsphere). The function of the Polylysine is to attract and immobilize microbial samples such as bacteria.

Poly-L-lysine is a natural homopolymer of the amino acid lysine. The general formula for Poly-L-lysine is —(C6H12N2O)n- where "n" is typically 25-30 subunits of lysine. The primary amines of each lysine subunit give the overall molecule a net positive charge. This positive charge electrostatically attracts the net negative charge found on most bacterial cell walls. Poly-L-lysine has historically been used as an antibacterial in food (GRAS status in the USA) and as a fixative in tissue culture to promote cell adherence.

Microsphere—A microsphere is typically any particle or bead with a large surface area to volume ratio which forms a colloid when mixed with an aqueous solution. Ideally, the particle can remain in solution for a significant amount of time (required to come in contact with the bacteria) allowing time to interact and attract with the bacteria. In addition, once sufficient time has elapsed to attract bacteria or other exemplary microorganism, the particle can then be extracted from the aqueous environment via an applied external force (e.g. magnetic field, centrifugation, filtration, electric field).

In one embodiment, the microspheres may be a protein microsphere, for example, a human serum albumin microsphere. In some embodiments, the microspheres are unstabilized microspheres that have not been stabilized, for example by treatment with a cross-linking agent, tanning agent (such as Cr+++ or other alkali metal tanning agent), or a fixative (such as an aldehyde, e.g., glutaraldehyde or formaldehyde). In other embodiments, the microbubbles may be stabilized. Microspheres which are unstabilized may advantageously be destroyed by solubilization with a detergent.

As used herein, microorganism is understood to include any prokaryotic microscopic organism (including bacteria) or eukaryotic microscopic organism (including protozoa, algae, yeasts and fungi), and/or viruses. The bacteria can include those generally known as pathogenic bacteria, such as, for example, species of Enterobacteriaceae, Vibrionaceae, *Bacillus, Escherichia, Streptococcus, Pseudomonas, Salmonella, Legionella, Enterobacter*, etc. In some embodiments, the bacteria are gram negative bacteria. In other embodiments, the sample is gram positive bacteria.

As used herein, a support is understood to include a solid formed by a polymeric material which has, on its surface, a large number of chemical groups necessary for fixing molecules of interest.

As used herein, quantifying is understood as determining in an exact manner the concentration or amount of the microorganism of interest in the sample. Semi-quantifying is understood as determining in an approximate manner the concentration of the microorganism of interest in the sample. Detecting is understood as determining the presence-absence of the microorganism of interest in the sample.

As used herein, a "sample" includes any sample that is suspected of containing the microorganism. The sample will generally be of a diagnostic, environmental and/or food origin, and in certain cases will be of biological fluids.

As used herein, the term "selection" includes both "negative" selection and "positive" selection. Negative selection processes are processes in which the unwanted components are bound to the functionalized affinity separation particles are isolated during the procedure, leaving the desired components in the sample. On the other hand, "positive" selection processes include separation processes in which the wanted components are bound to the functionalized affinity separation particles and isolated during the procedure. In certain embodiments, separation processes are used to achieve an enrichment or the desired sample or depletion of the undesired sample.

As used herein, detection may involve, for example, fluorescence assay, enzyme-linked immunosorbent assay (ELISA), optical microscope, electron microscope, or a combination thereof.

In some embodiments, the biological test sample includes a biological fluid. Biological fluids are typically liquids at physiological temperatures and can include naturally occurring fluids present in, withdrawn from, expressed or otherwise extracted from a subject or biological source. Certain biological fluids derive from particular tissues, organs or localized regions and certain other biological fluids can be more globally or systemically situated in a subject or biological source. Non-limiting examples of biological fluids include blood, serum and lymph, urine, cerebrospinal fluid, saliva, serosal fluids, plasma, lymph, mucosal secretions of the secretory tissues and organs, vaginal secretions, breast milk, tears, and ascites fluids such as those associated with non-solid tumors—are also suitable. Additional examples include fluids of the pleural, pericardial, peritoneal, abdominal and other body cavities, and the like. Biological fluids can further include liquid solutions contacted with a subject or biological source, for example, cell and organ culture medium including cell or organ conditioned medium, lavage fluids and the like. In other embodiments the biological sample is blood serum, plasma, or the supernatant of centrifuged urine.

In certain embodiments, exemplary poly-1 lysine compound and compositions suitable for capture of bacteria can include any suitable poly-1-lysine [HBr] compounds of varying molecular weight, including for example, compounds ranging from about 130,000 MW(vis), about 68,000 MW(vis), down to about 4,200 MW(vis) for the functionalization of the solid support material such as microparticles and/or microspheres. These exemplary composition has efficacy in isolating gram (+) and gram (−) bacteria. In certain embodiments, the compounds and compositions of the disclosure can be used in combination with other capture moieties, such as for example, polymyxin B, antilipid A, antigen, antiEcoli (pAb), lysozyme, deactivated lysozyme, ampicillin, anti-FLIC, cecropin, and bactenecin as needed to achieve detection, separation, concentration, depletion, and/or detection.

The present disclosure also provides a kit for the determination/detection/separation/concentration/purification of samples containing microorganisms. The scope of said determination/detection/separation/concentration/purification can be semiquantitative or quantitative; semiquantitative determination is understood as one in which the result is an estimation of the order of magnitude of the concentration of the microorganism of interest in the sample. The kit allows the selective capture of the microorganism of interest in aqueous, water and/or food samples, its concentration and separation from the remaining components of the sample, and its colorimetric detection, in a simple and rapid manner, in situ determination being possible. The kit uses vanco-PVA molecules directed against the microorganism of interest, immobilized on their surface, which in the supplied reaction media bind specifically to the microorganism of interest that is present or potentially present in the sample.

In one aspect, the disclosure provides a method of detecting microorganisms comprising steps of: (a) contacting a sufficient amount of polylysine moiety with an appropriate sample for an appropriate period of time to permit the formation of complexes between the microorganisms and polylysine complexes; (b) aggregate said complexes; and (c) detecting said complexes.

In one embodiment, the sensitivity of detection for the method can be at least as low as 10 colony forming units (cfu) of the microorganisms in one milliliter of solution. The exemplary method of the present invention is capable of detecting anywhere from about 20, 40, 60, 80, or 100 cfu/mL. In another embodiment, for viruses, the exemplary method of the present invention is capable of detecting concentrations at least as low as 10 plaque forming units per one milliliter of solution (pfu/mL) and upwards of about 100, 500, or 1000 pfu/mL.

In one embodiment, the microorganisms are pathogens. As used herein, pathogens are defined as any disease-producing microorganism. Pathogens include, but are not limited to, bacteria, viruses, mycoplasma, algae, amoeba, or other single-cell organisms. The bacteria may be either Gram positive or Gram negative, which may be captured and/or affinity separated. The bacteria can include, but are not limited to, *Staphylococcus aureus, Staphylococcus epidermidis*, coagulase negative staphylococci (CNS), *E. coli*, or Vancomycin Resistant Enterococci (VRE).

The sample to be tested can be a clinical sample, which may include, but is not limited to, bodily fluid samples, smear samples, or swab samples. The sample can also be taken from the environment, which may include, but is not limited to, environmental sources such as water, air, or soil. Additionally, the sample can be taken from food products, which may include, but is not limited to, liquid or solid foods that are processed, concentrated, or otherwise artificially modified. The present invention can be very beneficial to the food industry where sensitive detection of pathogens is desired. Samples, whether in solid, liquid, or gas form, can be prepared accordingly (e.g. dilution, dissolution, immersion) so as to render them in solution form for use in the present invention.

As used herein, bifunctional means the ability to engage in ligand-receptor, antibody-antigen, ionic, or metal-ligand interaction. Thus, bifunctional describes the types of specific interactions possible between the microparticle/microsphere and microorganisms in the sample. The bifunctional magnetic particles can be a conjugate of magnetic or non-magnetic micro or nanoparticles and a functional group.

In certain embodiments, the solid support can comprise a magnetic microsphere/microparticle. The magnetic particles may be composed of, but are not limited to, iron, noble metals (such as gold, silver, platinum, or palladium), cobalt, metal oxides, nickel, or alloys thereof. In one embodiment, the magnetic nanoparticles are iron-platinum (FePt), $SmCo_5$, $Fe_3O_4$, $Fe_2O_3$, FePd, CoPt, $Sm_xCo_y@Fe_2O_3$, $Sm_xCo_y@Fe_3O_4$, $M@Fe_2O_3$, or $M@Fe_3O_4$, whereby x=1 to 4, y=5 to 20, and M is a magnetic metal selected from the group consisting of cobalt, nickel, iron, and magnetic alloys thereof. In the embodiment described above involving $Sm_xCo_y@Fe_2O_3$, $Sm_xCo_y@Fe_3O_4$, $M@Fe_2O_3$, and $M@Fe_3O_4$, the symbol "@" merely indicates that the magnetic nanoparticles have a $Sm_xCo_y$ or M core and a $Fe_2O_3$ or $Fe_3O_4$ shell. Metals which can be magnetic are well known in the art. See Magnetic Nanoparticles Having Passivated Metallic Cores. The functional group may be an antibiotic, ligand, receptor, or metal complex.

In one embodiment, the sample can be a biological sample selected from the group consisting of blood, serum, serosal fluid, plasma, lymph, urine, cerebrospinal fluid, saliva, a mucosal secretion, a vaginal secretion, ascites fluid, pleural fluid, pericardial fluid, peritoneal fluid, abdominal fluid, culture medium, conditioned culture medium and lavage fluid.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The polylysine complex may be immobilized on the solid support using a variety of techniques known to those in the art, which are amply described in the patent and scientific literature.

In certain embodiments, the polylysine moiety can contain a detectable reporter moiety or label such as an enzyme, dye, radionuclide, luminescent group, fluorescent group or biotin, or the like. Any reporter moiety or label could be used with the methods disclosed herein so long as the signal of such is directly related or proportional to the quantity of antibody remaining on the support after wash. The amount of the second antibody that remains bound to the solid support is then determined using a method appropriate for the specific detectable reporter moiety or label. For radioactive groups, scintillation counting or autoradiographic methods are generally appropriate. Antibody-enzyme conjugates can be prepared using a variety of coupling techniques (by way of example, see Scouten, W. H. (1987) A survey of enzyme coupling techniques. Methods in. Enzymology 135, 30-65). Spectroscopic method can be used to detect dyes (including, for example, colorimetric products of enzyme reactions), luminescent groups and fluorescent groups. Biotin can be detected using avidin or streptavidin, coupled to a different reporter group (commonly a radioactive or fluorescent group or an enzyme). Enzyme reporter groups can generally be detected by the addition of substrate (generally for a specific period of time), followed by spectroscopic, spectrophotometric or other analysis of the reaction products. Standards and standard additions can be used to determine the level of antigen in a sample, using well-known techniques.

Standard recombinant DNA and molecular cloning techniques used in the examples are well known in the art.

While the present invention has been described in conjunction with specific embodiments set forth above, many alternatives, modifications and variations thereof will be apparent to those of ordinary skill in the art. All such alternatives, modifications and variations are intended to fall within the spirit and scope of the present invention.

EXAMPLES

While various embodiments of the present invention have been described above, it should be understood that they have been presented by way of example only, and not limitation. The following non-limiting examples are illustrative of the invention.

Example 1

Demonstration of efficacy of an exemplary Polylysine-coated albumin microsphere which is capable of capturing Gram positive and negative microorganisms.

Synthesis of a Polylysine-Coated Albumin Microsphere

Production of 1% Human Serum Albumin (HSA) Microspheres 20 mL of albumin (Human) 5%, USP [Talecris] was diluted to 1% with the addition of 80 mL of 0.9% (w/w) sodium chloride solution. 20 mL of the 1% HSA was then aliquoted in five separate 60 cc polypropylene test tubes [Falcon]. In series, each test tube was heated to 73.5° C. in a 80° C. water bath, then immediately sonicated with a ½" diameter probe at 20,000 hertz at 80% power for 10 seconds [Digital Sonifier model 450; Branson]. Each sonicated solution was put on ice immediately and allowed to cool below 30° C. Once cool, all five sonicated solutions were pooled into a 150 cc flexible container [Flexboy; Stedim]. The Falcon test tubes were rinsed with saline (twice) and rinses added to the pooled, sonicated solution in the Flexboy container. A 10% solution of sodium azide was then added to the pooled solution to a final concentration of 0.05% (w/w) to act as a preservative. The contents of the Flexboy bag were then gently mixed and stored upright in a refrigerator.

To wash excess albumin in solution away from the microspheres, the solution was allowed to settle in the refrigerator overnight. During this time, the microspheres rose to the top of the solution. The Flexboy bag was then (carefully) removed from the refrigerator and the liquid portion of the solution (non-microsphere) drained from the Flexboy bag. Approximately 50 mL of cold, air saturated Phosphate Buffered Saline (PBS)/0.2% Polyvinyl alcohol (PVA) was added into the Flexboy bag and gently mixed to resuspend the microspheres. The entire contents of the Flexboy bag was then drained into a 60 cc plastic syringe [Becton Dickinson] fitted with a 2-way plastic stopcock. The solution was then spun in a refrigerated centrifuge [Sorvall RT6000B] at 1000 rpms for 3 minutes at 5° C., at which time the microspheres rose again to the top of the solution. The non-microsphere solution was drained through the stopcock fitted on the bottom of the syringe, then approximately 50 cc of cold, air-saturated PBS/PVA was added to the microspheres to gently resuspend the microspheres again. The centrifuge-drain-resuspend cycle was repeated twice more for a total of three separate washes. The final suspension volume was 30 cc.

Acetylation of Polylysine 32 mg of poly-L-lysine HBr (average molecular weight=68,300; Sigma] was dissolved in 2 mL of PBS. To add a protected sulfhydryl to the polylysine, 52 µL of 6.5 mg/mL$_{(DMSO)}$ SATA [Pierce] was added and vortexed immediately. The reaction was allowed to proceed for 2 hours at room temperature. This should yield approximately 3 SATA per molecule of polylysine.

After two hours, the reaction was transferred into a centrifugal filter device [Ultra 30K MWCO; Amicon] and 4× washed with 4 mL of PBS under centrifugation. The final volume of the washed reaction was approximately 0.160 mL.

To deprotect the sulfhydryls, 16 µL of a 500 mM solution of Hydroxylamine HCl [Pierce] was added to the polylysine in/SATA solution, then allowed to react for 2 hours at room temperature. The reaction was 4× washed with PBS/10 mM EDTA under centrifugation. The final volume of the washed reaction was left at 4 mL.

Activation of Microspheres with sSMCC 10 mg of sulfo-SMCC powder [Pierce] was transferred directly into 10 cc of 1% HSA Microspheres under constant vortex. This reaction was allowed to proceed on ice for 30 minutes with intermittent mixing to keep the microbubbles in suspension throughout the reaction. After ½ hour, the microspheres were 3× washed in a 30 cc syringe (with stopcock) with 20 cc PBS/PVA under centrifugation as previously described. After the final wash, all liquid was drained from the syringe to leave only a pure layer of microspheres behind in the syringe.

Addition of Polylysine-SH to sSMCC-Microspheres

Immediately after the final wash of the polylysine-SH, all 4 mL of the solution was added to the layer of pure sSMCC-Microspheres under constant vortex. This reaction was allowed to proceed on ice for 2 hours with intermittent mixing to keep the microspheres in suspension. After 2 hours, the microspheres were 3× washed in a 30 cc syringe (with stopcock) with 20 cc PBS/PVA under centrifugation as previously described. After the final wash, the microspheres were resuspended in 10 cc of PBS/PVA. The microspheres were then stored in a refrigerator until needed.

Attraction of Bacteria with Polylysine-Coated Microspheres

Preparation of Gram Positive and Negative Bacteria

Cultures of *Escherica coli*0157:h7 (gram negative), *Proteus mirabilis* (gram negative), *Staphylococcus epidermidis* (gram positive), and *Streptococcus gallolyticus* (gram positive) were initiated from known colony plates and incubated in Nutrient broth (*P. mirabilis* only) [IPM Scientific] or LB broth (all others) [IPM Scientific] at 37° C. overnight. 1 mL of each bacterial solution was transferred into separate 1.5 mL plastic test tubes and centrifuged at 10,000 rpms for 10 minutes at room temperature. The centrifugation formed a pellet of bacteria at the bottom of each test tube. All liquid above the bacterial pellet was suctioned off and replaced with 1 mL of fresh PBS. Each bacterial pellet was resuspended in the PBS by vortex. The cells were then stained by adding 2 µL of Syto 13 green fluorescent nucleic acid stain [Molecular Probes], allowed to incubate for ½ hour in the dark at room temperature, then 3× washed with 1 mL PBS by centrifugation. Cells were resuspended in a final volume of 1 mL PBS.

Addition of Polylysine-Coated Microspheres to Bacteria

200 µL of polylysine-coated microspheres were added separately to 200 µL of the *E. coli*, *P mirabilis*, *S epidermidis*, and *S gallolyticus* cultures, vortexed, then allowed to react for ½ hour in the dark at room temperature. As a negative control, 1% HSA microspheres not coated with polylysine were added in the same ratios to the 4 bacteria and incubated under the same conditions. After ½ hr. both non- and polylysine-coated samples were 4× washed with PBS/PVA by centrifugation and recovery/wash of the microspheres that floated to the top. After the fourth wash, microspheres were resuspended in a final volume of 500 µL.

Results

10 µL of each sample was transferred to a glass microscope slide and overlaid with a glass coverslip. Each sample was examined first under visible light to verify the presence and integrity of the microspheres, then under dark field (illuminated with a filtered mercury lamp) to view fluorescence. Visual observations are presented in Table 01:

TABLE 01

Presence of Fluorescent Bacteria with Polylysine-coated Microspheres

| Sample | Bacteria | Microsphere Observation | Bacteria Observation |
|---|---|---|---|
| Microspheres + polylysine | *E. coli*0157:h7 | clumpy | many fluorescent bacteria present |
| Microspheres + polylysine | *P. Mirabilis* | clumpy | many |
| Microspheres + polylysine | *S. epidermidis* | clumpy | many |
| Microspheres + polylysine | *S. gallolyticus* | clumpy | many |
| Microspheres only (negative control) | *E. coli*0157:h7 | monodisperse | scant |

TABLE 01-continued

Presence of Fluorescent Bacteria with Polylysine-coated Microspheres

| Sample | Bacteria | Microsphere Observation | Bacteria Observation |
|---|---|---|---|
| Microspheres only (negative control) | *P. Mirabilis* | monodisperse | scant |
| Microspheres only (negative control) | *S. epidermidis* | monodisperse | scant |
| Microspheres only (negative control) | *S. gallolyticus* | monodisperse | scant |

From the table above, it is apparent that when bacteria are exposed to albumin microspheres that have either been coated with polylysine in or left bare (uncoated), that all 4 bacteria in this experiment are preferentially attracted to the polylysine in-coated microspheres.

Based on the data above, the presence of polylysine on the surface of an albumin microsphere is capable and is effective in capturing gram positive and gram negative bacteria in solution.

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

What is claimed is:

1. A synthetic polymer solid support complex of the general formula (I):

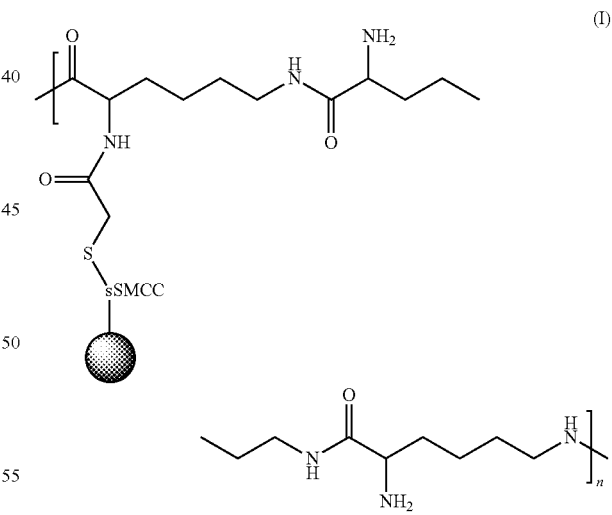

wherein n is 10 to 100, comprising a synthetic polymer comprising repeating monomer units of polylysine, a linker, and a solid support, wherein the linker is sulfo-succinimidyl-4-(N-maleimidomethyl)cyclohexane-1-carboxylate (sSMCC), and wherein the synthetic polymer forms a complex with the solid support via the linker and said synthetic polymer-solid support complex is effective in binding microorganism.

2. The synthetic polymer solid support complex of claim 1, wherein the solid support comprises a microsphere.

3. The synthetic polymer solid support complex of claim 2, wherein the microsphere comprises a coating of human serum albumin.

4. A composition comprising synthetic polymer solid support complex of claim 2.

5. The composition according to claim 4 wherein the microsphere is a magnetic microsphere.

6. The composition of 4 wherein the molecular weight of the poly-L-lysine is from about 4200 to about 130,000 kd.

7. The synthetic polymer solid support complex of claim 1, wherein the solid support comprises magnetic particles that comprises iron, noble metals, cobalt, metal oxide, nickel, or alloys thereof.

8. A method of detecting, capturing, concentrating, or depleting microorganisms in a sample, comprising:
(a) providing synthetic polymer solid support complexes of claim 1, each comprising Poly-L-Lysine attached to a microsphere;
(b) contacting the sample with the synthetic polymer solid support complexes, whereby the synthetic polymer solid support complexes bind to the microorganisms,
(c) separating the synthetic polymer solid support complexes in said sample; and
(d) detecting, capturing, concentrating, or depleting the microorganisms that are bound to the synthetic polymer solid support complexes.

9. The method of claim 8, wherein the microorganisms are bacteria.

10. The method of claim 9, wherein the microorganisms are gram-positive or gram-negative bacteria.

11. The method of claim 9, wherein the microorganisms are selected from *Staphylococcus epidermidis*, *Streptococcus gallolyticus*, *Escherica coli*, and *Proteus mirabilis*.

12. The method of claim 8, wherein the synthetic polymer solid support complex further comprises a fluorescent stain.

13. The method of claim 12, wherein the fluorescent stain is a green fluorescent nucleic acid stain.

14. The method of claim 8, wherein the microsphere comprise a coating of human serum albumin.

15. The method of claim 8, wherein Poly-L-Lysine is attached to the microsphere via an avidin or streptavidin linkage.

16. The method of claim 15, wherein the Poly-L-Lysine is attached to the microsphere via sulfo-succinimidyl-4-(N-maleimidomethyl)cyclohexane-1-carboxylate (sSMCC).

17. The method according claim 8, wherein the microsphere is a magnetic microsphere and the separating is achieved by aggregation of the microorganism-bound synthetic polymer solid support complexes under a magnetic field.

18. The method of claim 8, wherein the sample is a body fluid selected from the group consisting of urine, blood, serum, plasma, spinal fluid, synovial fluid, saliva, urine, semen, cell and tissue homogenates.

19. The process of claim 18, wherein the deprotecting agent is hydroxylamine hydrochloride.

20. A process for preparing a synthetic polymer solid support complex of general formula (I) comprising the steps:

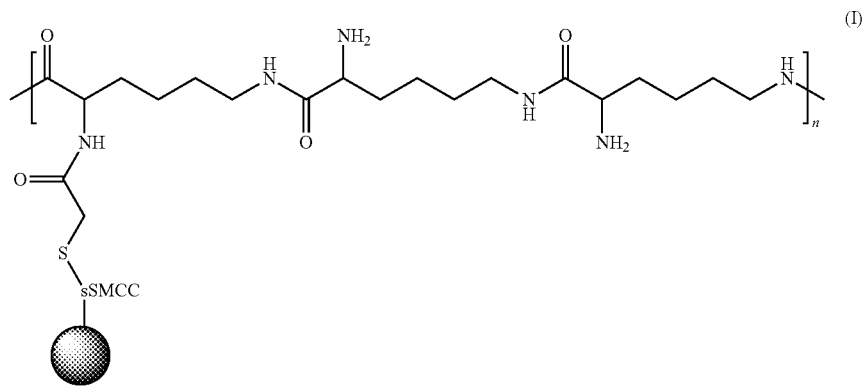

wherein n is 10 to 100,
a) reacting polylysine with (N-succinimidyl S-acetylthioacetate) (II) to give the compound of formula (III):

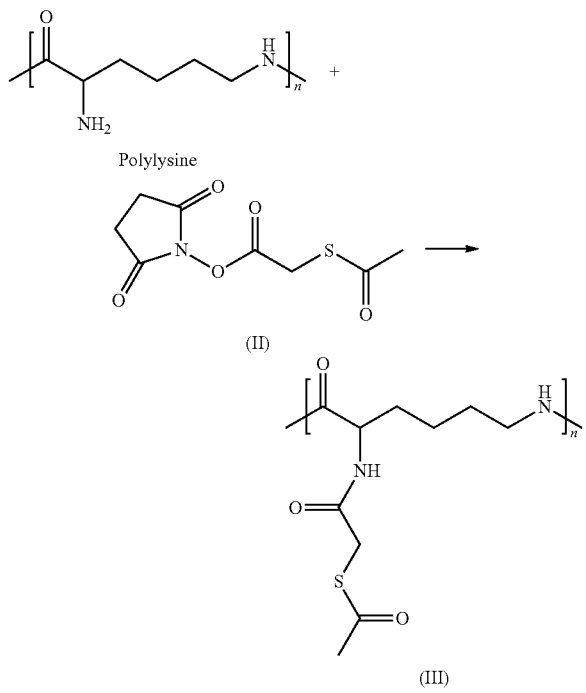

b) reacting the compound of formula (III) from step a) with a deprotecting agent to give the compound of formula (IV):

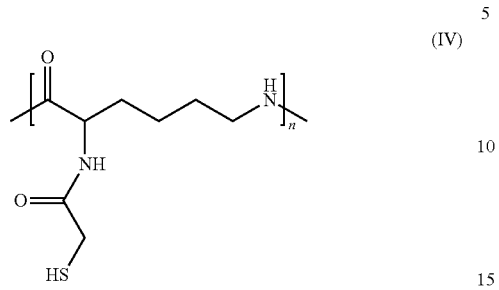

(IV)

c) reacting sulfo-succinimidyl-4-(N-maleimidomethyl) cyclohexane-1-carboxylate (sSMCC) with human serum albumin coated microspheres to produce the compound of formula (V):

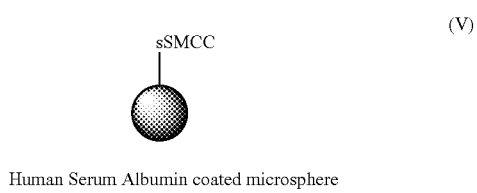

(V)

Human Serum Albumin coated microsphere d) reacting the compound of formula (IV) from step b) with the compound of formula (V) from step c) to produce the synthetic polymer solid support complex of general formula (I).

\* \* \* \* \*